United States Patent
Rood et al.

(10) Patent No.: US 11,832,599 B2
(45) Date of Patent: Dec. 5, 2023

(54) INSECT BREEDING

(71) Applicant: Ynsect NL R&D B.V., Ermelo (NL)

(72) Inventors: Nico Rood, Ermelo (NL); Johannes Ignatius Maria Calis, Ermelo (NL)

(73) Assignee: Ynsect NL R & D B.V., AB Ermelo (NL)

( * ) Notice: Subject to any disclaimer, the term of this patent is extended or adjusted under 35 U.S.C. 154(b) by 0 days.

(21) Appl. No.: 16/649,013

(22) PCT Filed: Sep. 19, 2018

(86) PCT No.: PCT/NL2018/050615
§ 371 (c)(1),
(2) Date: Mar. 19, 2020

(87) PCT Pub. No.: WO2019/059760
PCT Pub. Date: Mar. 28, 2019

(65) Prior Publication Data
US 2020/0288685 A1    Sep. 17, 2020

(30) Foreign Application Priority Data
Sep. 20, 2017 (NL) .................................... 2019586

(51) Int. Cl.
*A01K 67/033* (2006.01)
*A01K 1/03* (2006.01)

(52) U.S. Cl.
CPC .............. *A01K 67/033* (2013.01); *A01K 1/03* (2013.01)

(58) Field of Classification Search
CPC ....... A01K 67/033; A01K 1/03; A01K 1/0047
See application file for complete search history.

(56) References Cited

U.S. PATENT DOCUMENTS

2013/0319334 A1* 12/2013 Newton ................. A01K 29/00
119/6.5
2015/0008163 A1* 1/2015 Nimmo .................. B07B 13/04
209/17
(Continued)

FOREIGN PATENT DOCUMENTS

CA    2979709 A1 * 9/2016 ........... A01K 67/033
FR    3034622 A1 * 10/2016 ........... A01K 67/033
(Continued)

OTHER PUBLICATIONS

International Search Report and Written Opinion of PCT/NL2018/050615, dated Jan. 18, 2019, 14 pages.

*Primary Examiner* — Monica L Perry
*Assistant Examiner* — Aaron M Rodziwicz
(74) *Attorney, Agent, or Firm* — Blank Rome LLP

(57) ABSTRACT

An insect breeding system (1) for the breeding of insect larvae, comprising a multitude of similar, stackable crates (20, 30, 40), a climate housing (2), and crate stacking equipment (3), wherein the multitude of similar, stackable crates each have a same width (D1), a same length (D2), a same corner structure (4) that comprises complementary lower elements (5) and upper elements (6), configured to allow stacking of the crates on top of each other by allowing the upper elements of a lower crate to interact with lower elements of an upper crate, and a containment area (7) defined by the width, the length, and a height of the crate.

14 Claims, 8 Drawing Sheets

(56) References Cited

U.S. PATENT DOCUMENTS

| | | | | |
|---|---|---|---|---|
| 2015/0223496 A1* | 8/2015 | Kitazumi | ................ | C05F 17/05 |
| | | | | 119/6.5 |
| 2016/0066552 A1* | 3/2016 | Arsiwalla | ............ | A01K 1/0047 |
| | | | | 119/6.5 |
| 2018/0007875 A1* | 1/2018 | Hall | ......................... | A01K 7/02 |
| 2018/0064079 A1* | 3/2018 | Hasa | .................... | A01K 67/033 |
| 2018/0271074 A1* | 9/2018 | Sobecki | .................... | B07B 1/46 |
| 2018/0369867 A1* | 12/2018 | Sobecki | .................... | B07B 1/06 |
| 2019/0387704 A1* | 12/2019 | Hall | .................... | A01K 67/033 |
| 2021/0127644 A1* | 5/2021 | Ritz | .................... | A01K 67/033 |
| 2021/0144978 A1* | 5/2021 | Staal | .................. | B65D 21/0215 |

FOREIGN PATENT DOCUMENTS

| | | | | |
|---|---|---|---|---|
| FR | 3034623 A1 * | 10/2016 | ........... | A01K 67/033 |
| WO | WO-2014/171829 A1 | 10/2014 | | |
| WO | WO-2016/153338 A1 | 9/2016 | | |
| WO | WO-2016153339 A1 * | 9/2016 | ........... | A01K 67/033 |
| WO | WO-2016153340 A2 * | 9/2016 | ........... | A01K 67/033 |
| WO | WO-2017/007310 A1 | 1/2017 | | |
| WO | WO-2018231053 A1 * | 12/2018 | ............. | B65D 85/50 |

\* cited by examiner

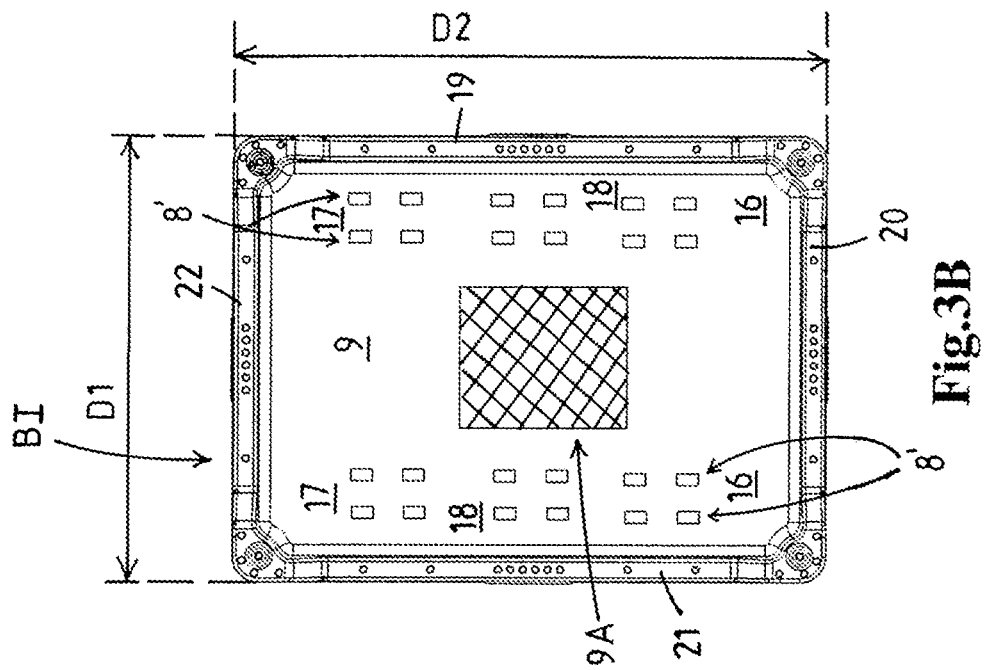
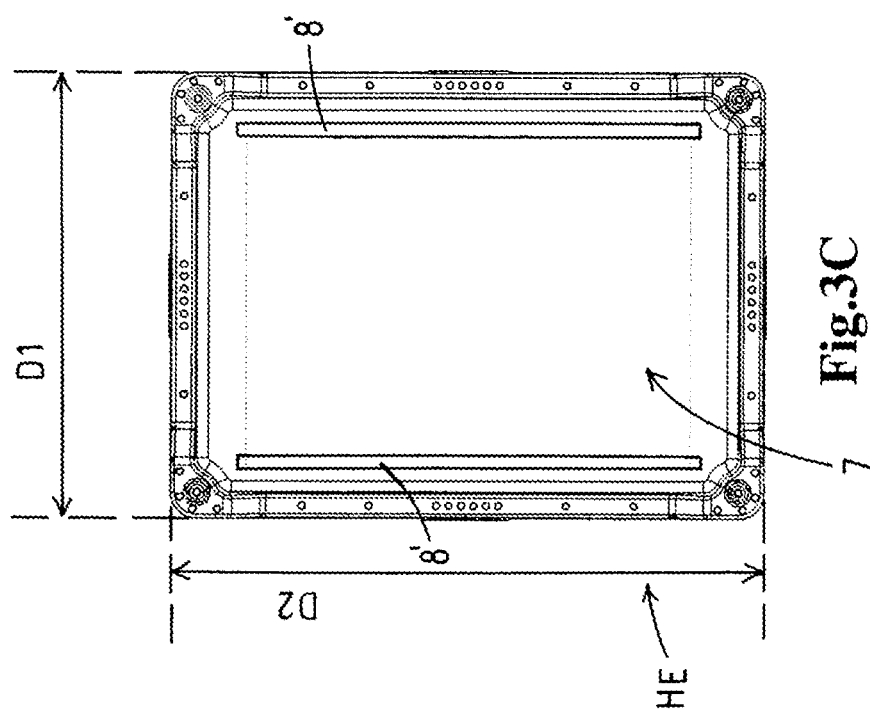

Fig. 3E
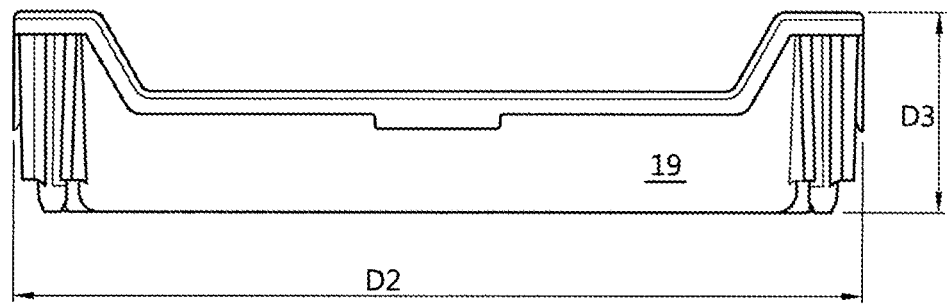
Fig. 4A
Fig. 4B
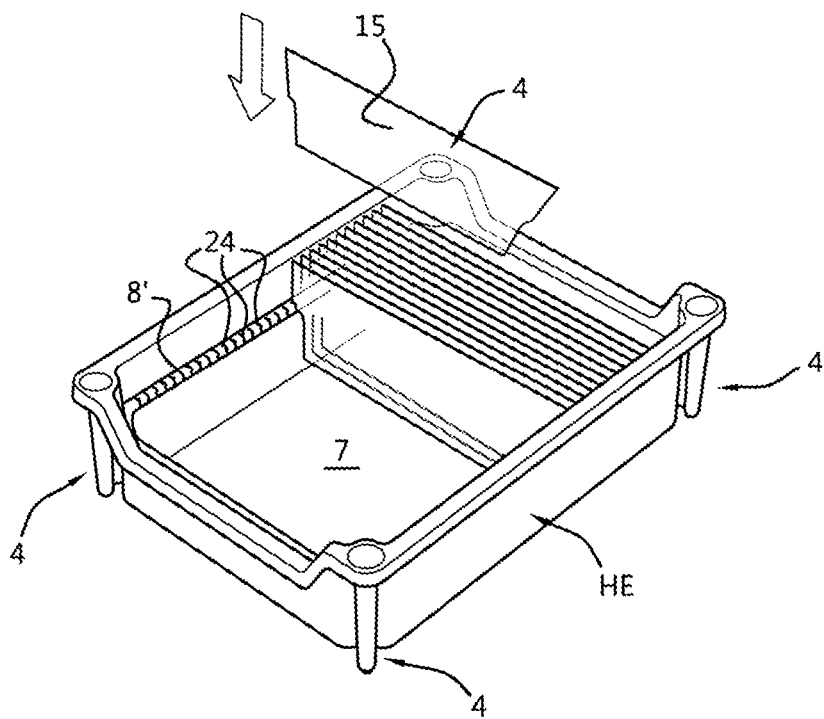

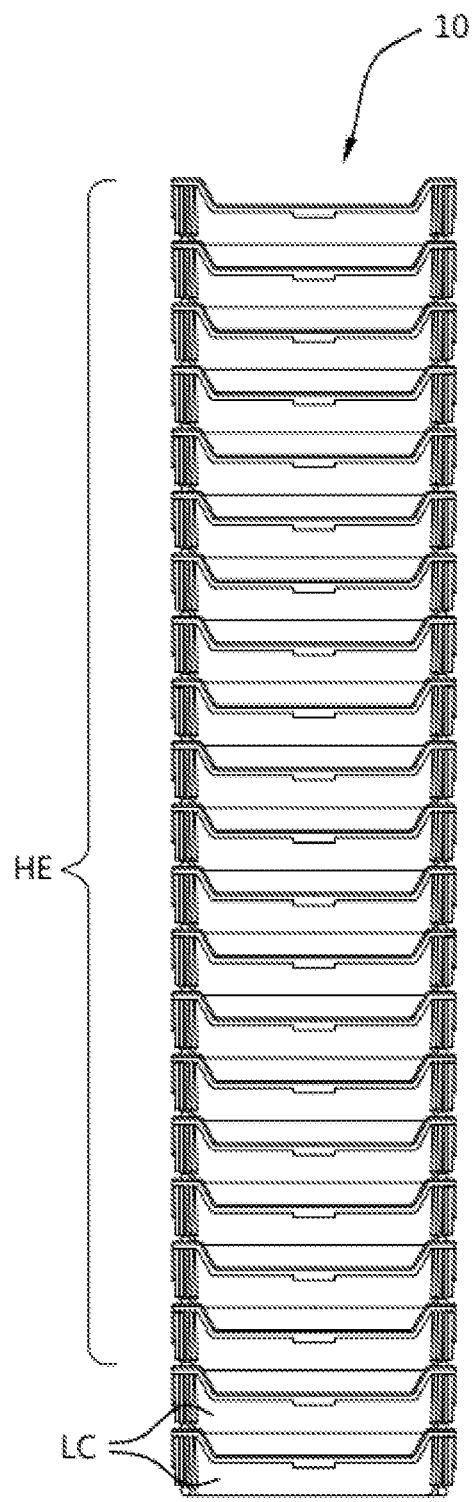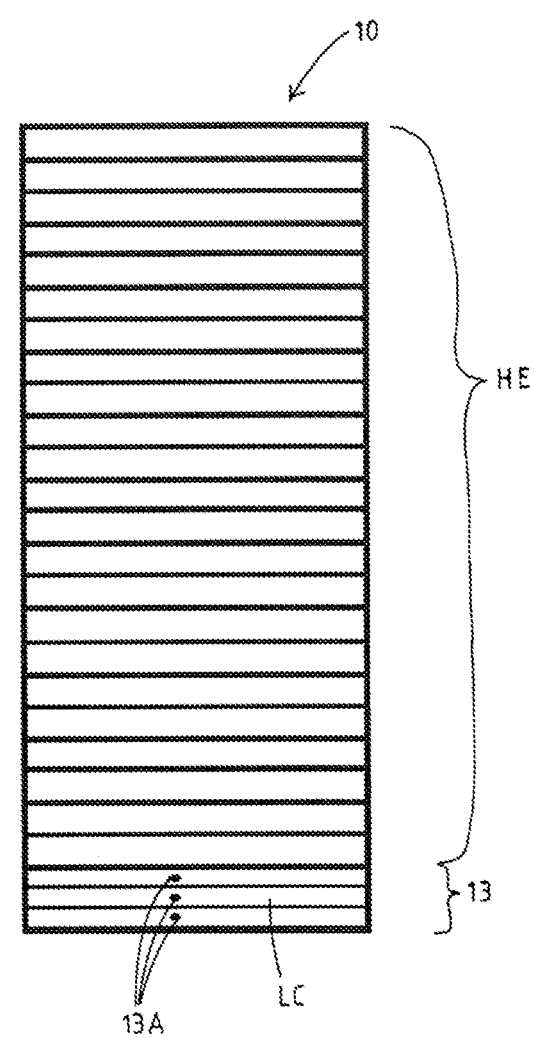
Fig.5A  Fig.5E

INSECT BREEDING

RELATED APPLICATIONS

This application is a national phase of PCT/NL2018/050615, filed on Sep. 19, 2018, which claims the benefit of Netherlands Application No. 2019586, filed on Sep. 20, 2017. The entire contents of those applications are hereby incorporated by reference.

FIELD OF THE INVENTION

The present invention relates to an insect breeding system and a method for the breeding of insects.

BACKGROUND OF THE INVENTION

Mature larvae of different types of insects are commercially available and can be used as protein rich food for animals, e.g. cats and dogs, or humans. For the semi-near future, it is foreseen that larvae of insects will be accepted as human food by the general public, urging industrial-size breeding facilities for larvae of insects to be developed.

Four life cycle stages can be identified for most types of insects. Mother insects lay eggs, which eggs define a first life cycle stage. From the eggs, baby larvae are born, which baby larvae define a second life cycle stage. These baby larvae grow into mature larvae, a process that in the art is called rearing, and ultimately become cocoons or pupae, defining the third life cycle stage. From a cocoon, an adult insect pops, the adult insects defining the fourth life cycle stage.

At the moment, for nutrient purposes, the mature larvae are commercially most relevant. To obtain these mature larvae, adult insects including egg-laying mothers are needed. Eggs laid by these mothers are hatched to obtain baby larvae, and the baby larvae are reared into mature larvae. For commercial purposes, a portion of the mature larvae population is kept to become adult insects for the breeding of a further generation, while another portion of the mature larvae population is sold.

In known breeding facilities, adult insects including egg-laying mothers are held in containers, in which containers the egg-laying mothers receive food and spawn their eggs. The eggs hatch, and the baby larvae mature into mature larvae in the same container, from which the mature larvae are removed to serve as protein rich food. A problem conceived in such containers is that adult insects tend to eat the eggs, lowering the breeding efficiency.

WO 2017007310 A1, of the same applicant, presents an insect breeding facility for the industrial scale production of mature larvae from egg-laying mothers. WO 2017007310 A1 proposes an insect breeding facility where the eggs can efficiently be separated from the mothers, using a spawning container comprising a plurality of spawn structures, in which spawn structures egg-laying mothers will spawn their eggs during an egg-laying lifetime, and the use of hatching containers, in which the eggs are allowed to hatch into baby larvae and subsequently mature into mature larvae during a hatching and tending time.

SUMMARY OF THE INVENTION

It is an object of the present invention to provide an alternative insect breeding system.

Therefore, an insect breeding system is presented for the breeding of insect larvae, comprising a multitude of similar, stackable crates, a climate housing, and crate stacking equipment;

wherein the multitude of similar, stackable crates each have:
  a same width;
  a same length;
  a same corner structure that comprises complementary lower elements and upper elements, configured to allow stacking of the crates on top of each other by allowing the upper elements of a lower crate to interact with lower elements of an upper crate;
  a containment area defined by the width, the length, and a height of the crate,
wherein each crate can be tuned to one of the following crate types, e.g. by providing the crates with suitable holders, and/or by removing at least a part of a bottom thereof, such that each crate can be tuned to one of the following crate types; and
wherein the below three crate types are part of the insect breeding system:
  an egg crate, suited to contain insect eggs in the containment area thereof, e.g. allowing the hatching of said insect eggs into baby larvae;
  a larvae crate, suited to contain larvae, e.g. baby larvae, and larvae food in the containment area thereof, allowing the rearing of such larvae;
  an insect crate, suited to contain live adult insects including mother insects and insect food in the containment area thereof, allowing the mothers to lay eggs;
wherein the climate housing is provided with one or more stacks of said similar crates, each stack having a stack height of at least five, such as at least eight, e.g. at least ten crates; and
wherein the crate stacking equipment is configured to, i.e. allows, each of the similar crates, i.e. each of the egg, larvae and insect crate types, to be arranged as a part of the one or more stacks, e.g. on top of a stack or below a stack, individually and independently.

An advantage of this system is that it is possible to operate the insect breeding system more efficiently.

An advantage of stacking the crates, is that space in the climate housing is used more efficiently, reducing building and operational costs for insect farmers.

A further advantage of the invention, providing crates that are similar and stackable allows for easier crate handling, as will become more apparent when embodiments of the invention are described in more detail.

An advantage of the present invention is that a scalable system is presented, wherein the quantity of live insects can easily be up-scaled or down-scaled, using the same equipment.

The insect breeding system comprises a multitude of similar, stackable crates, a climate housing, and crate stacking equipment.

As described in the above, the four life cycle stages of an insect comprise an egg stage, a larvae stage, a cocoon or pupae stage, and an adult stage. The present invention relates to an insect breeding system for the breeding of insect larvae. It is conceivable that such larvae may not be present at all times in the insect breeding system. It is foreseen that, for example, at times, the insect breeding system only comprises adult insects and eggs. The insect breeding system will then only comprise larvae when the eggs are hatched.

The climate housing of the insect breeding system preferably provides different insect breeding zones for different stages of insect breeding. For example, to stimulate egg-laying mothers to spawn their eggs, other environmental conditions, such as temperature and humidity, may be optimal compared to optimal conditions for hatching of the eggs and/or rearing of the larvae. The climate housing may provide at least four climate zones: one zone to provide optimal conditions for egg-laying mothers to spawn eggs; one zone to provide optimal conditions for eggs such that the eggs can be hatched, one zone for the rearing of larvae, and one zone for the cocoons. Two or more zones may have similar environmental conditions, for example the zone in which the larvae are reared and the zone wherein the egg-laying mothers are contained. It is noted that the climate housing may provide even more zones, e.g. when different types of insect are bred in the same climate housing, or additional zones may be present, e.g. for storing insect food and/or for retaining mature larvae of distinct ages. The climate housing may also provide only one environmental zone, wherein the crates are protected from the environment, and where e.g. predators of insects are kept away from the crates. There may also be different climate housings for one or more different steps of the insect breeding process.

The climate housing according to the invention is provided with one or more stacks of said same crates, each stack having a stack height of at least five, such as at least eight, e.g. at least ten crates. It is noted that also loose crates, i.e. crates that are not stacked, e.g. crates that are compatible with the similar stackable crates, or crates that are non-compatible with the similar stackable crates, may be present in the climate housing, and/or that stacks with a stack height lower than five may be present in the climate housing. To enable an efficient breeding process, however, at least one stack having a stack height of at least five should be present. Preferably, the climate housing comprises many stacks, e.g. a hundred of more, each stack having a stack height of 10 or more, e.g. having an absolute height of 1.5 meter or more, to make optimal use of an internal volume of the climate housing. Thereby, advantageously, the space of the climate housing is optimally used and operational costs for insect farmers, e.g. in terms of building rent and/or energy costs are reduced.

The crate stacking equipment is configured to handle each of the same crates, i.e. each of the egg crates, the larvae crates and the insect crates to be arranged as a part of the one or more stacks, e.g. on top of a stack or below a stack, individually and independently. The crate stacking equipment is able to stack all of the crates, i.e. all three types, if present, in any desired order, as the crates are all similar and stackable. The crate stacking equipment is for example suited to place a crate on top of or below an existing stack, to create a stack from multiple crates, to take one crate out of a stack, e.g. from below the stack, or to place a crate in between a stack. The crate stacking equipment may be configured to handle one crate at the time, or may be configured to handle multiple crates simultaneously. The crate stacking equipment may for example comprise human operators, robots, fork-lift, or other crate stacking equipment.

For example, egg crates may be stacked on top of each other.

For example, insect crates may be stacked on top of each other.

For example, larvae crates may be stacked on top of each other.

For example, an egg crate may be stacked on top of a larvae collection crate.

For example, an insect crate may be stacked on top of an egg collection crate.

The insect breeding system comprises a multitude of similar, stackable crates. One may say that the crates define a modular system, like LEGO® pieces, wherein each crate is compatible with the other crates. They can all be stacked on top of each other in any desired order. To allow this stackability, each crate has a same width, a same length, and a same corner structure that comprises complementary lower elements and upper elements, configured to allow stacking of the crates on top of each other by allowing the upper elements of a first, lower, crate to interact with lower elements of a second, upper, crate. Vice versa, the first crate, having a same corner structure as the second crate, may be placed on top of the second crate. Note that the width, the length, and the corner structure are the same for each type of crate, but that the crates need not be identical. It is foreseen that the crates are for example made with an injection moulding system. As a further example, sidewalls of the crates, although having a same width and length, may be different. For example, they may have a different shape, may have different cut-outs, may have a different colour, may have a different height, may have a different thickness, and so on.

Although the crates are similar, at least three different types of crates may be distinguished. The types of crates may for example be mutually different by making a modification to a containment area thereof, such that the length, width, and corner structure of the types of crates are the same, but the inner side is different. The insect breeding system may comprise an egg crate, suited to contain insect eggs in the containment area thereof, a larvae crate, suited to contain larvae and larvae food in the containment area thereof and allowing the rearing of such larvae, and an insect crate, suited to contain live adult insects including mother insects and insect food in the containment area thereof, allowing the mothers to lay eggs. The insect breeding system comprises at least two of said three types of crates, i.e. all three types of crates, or an larvae crate and an egg crate, or an egg crate and a mother crate, or a mother crate and larvae crate. Besides the three mentioned types of crates, a cocoon crate may further be present in the insect breeding system, suited to allow the popping of cocoons into adult insects.

Possible modifications to tune the crates into mutually different crate types may be the provision of suitable holders, e.g. for holding a spawn structure and/or the modification of at least a part of a bottom thereof, e.g. a removal of a part of the bottom.

The crates may be open-bottomed, bottomed, or close-bottomed. An open-bottomed crate has an open bottom structure and may e.g. be bottomless, or may for example have a lattice or sieve structure with openings in between the lattice or sieve structure. A bottomed crate has a bottom structure, although one or more openings may be provided in the bottom of the crate. For example, a multitude of small openings may be provided in the bottom of a bottomed crate, or a large opening may be provided that is covered with a sieve or lattice structure. A close-bottomed crate preferably has a fully closed bottom, without any openings in it.

The stack of said same crates may comprise multiple crates of the same type, stacked on top of each other, or may comprise a mixture of at least two types of crates. For example, the stack of crates may comprise a multitude of adult insect crates, a multitude of larvae crates, a mixture of adult insect crates and one or more egg crates, a mixture of egg crates and one or more larvae crates, and/or a mixture of egg crates, larvae crates, and adult insect crates.

The length of the crates is the same and may for example be between 40 cm and 150 cm, such as between 60 cm and 120 cm.

The width of the crates is the same and may for example be between 30 cm and 100 cm, such as between 40 cm and 80 cm. Preferably, the width of the crates is smaller than the length of the crates.

The height of the crates may be different for different types of crates. The height may for example be between 5 cm and 40 cm, such as between 10 cm and 30 cm. Preferably, the height of each crate is smaller than its length and its width.

The corner structure of the crates preferably allows for a direct stacking, i.e. wherein a first crate and a second crate are stacked directly on top of each other. It is however conceivable that in one or more phases of the insect breeding process, the inserts are arranged between two respective crates, such that the crates are stacked but indirectly. For example, when rearing the larvae, a large amount of heat may be generated. To dissipate this heat, depending on the configuration of the crate, it may be desired to create a distance between two stacked crate; providing an insert between them, and stacking them on top of each other with an insert in between them. The insert may for example be of a frame-like configuration, or may for example comprise four corner pieces or tubes.

In embodiments, the upper crate of the stack may be covered with a lid or an empty crate, to prevent the escape of insects or larvae contained in said upper crate.

In embodiments, the side walls of the crates have a uniform height, an upper edge of the side walls being arranged substantially parallel to a lower edge of the side wall, the upper edge and the lower edge being straight. This helps to keep the larvae or the insects contained in the crate. Preferably, in such embodiments, the side walls of the crates comprise openings, e.g. covered with a sieve, to allow oxygen and/or fresh air to reach the larvae or the insect in the crates. Advantageously, in such embodiments the entry of other organisms, e.g. other insects or animals, from outside of the crate into the containment area of the crate is made more difficult or prevented.

In embodiments, side walls of the crates comprise recessed portions along the upper edge thereof, allowing fresh air and/or oxygen to enter the containment area of the crate. In such embodiments, it is preferred when inner walls of the crates are very smooth, to prevent larvae or insects to escape from the crate via said recessed portions.

In an embodiment, the stack comprises a multitude of crates modified in that they have an open bottom structure, and at least one collection crate, having a closed bottom structure, allowing insect of a particular life cycle, arranged in the open-bottomed crates, to fall through the open bottom structure thereof, said insect of said life cycle being collected in the collection crate. The particular life cycle of the insect may for example be the egg life cycle stage or the larvae life cycle stage.

An advantage of providing a collection crate below an open-bottomed crate is that it allows for very efficient collection of insect life cycles of stages, as a second life cycle of insects is automatically separated from a first life cycle of insects when they fall through the open bottom. Hence, different life cycles of insects can be easily harvested.

In embodiments, the stack comprises a multitude of crates of the egg crate type, modified in that they have an open bottom structure, and at least one collection crate of the larvae crate type, having a closed bottom structure, such that the larvae hatching from the eggs contained in the open-bottomed egg crate, e.g. the hatching egg crate, are able to fall through the open bottom structure of egg crate, said larvae being collected in the larvae collection crate. A multitude of hatching egg crates may be stacked on top of each other, with one larvae collection crate below the stack of hatching egg crates.

In embodiments, the stack comprises a multitude of crates of the insect crate type, modified in that they have an open bottom structure, and at least one collection crate of the egg crate type, having a closed bottom structure, such that the eggs spawned by mother insects contained in the open-bottomed insect crate are able to fall through the open bottom structure of the insect crate, said eggs being collected in the egg collection crate. A multitude of open-bottomed insect crates may be stacked on top of each other, with an egg collection crate below the stack, or one egg collection crate may be provided below each open-bottomed insect crate.

In an embodiment, the insect breeding system comprises a hatching stack with a multitude of egg crates and at least one larvae crate, wherein the egg crates are embodied as hatching egg crates for the hatching of said insect eggs into baby larvae, the hatching egg crates being modified in that they have an open bottom structure, wherein the larvae crate is embodied as a larvae collection crate that has a closed bottom structure, and wherein the hatching egg crates are arranged on top of each other and the larvae collection crate is arranged below said hatching egg crates such that baby larvae hatching from the eggs contained in the hatching egg crates are able to fall through the open bottom structure of the multitude of stacked hatching egg crates, said baby larvae being collected in the larvae collection crate, e.g. on the closed bottom structure thereof.

An advantage of this embodiment of the invention, is that one needs less larvae crates than hatching egg crates, reducing the number of crates in the system, and thus making operation of the system cheaper. This allows for the efficient use of ground floor area of the climate housing by stacking the multitude of hatching egg crates on top of each other.

A further advantage is that this embodiment allows for very efficient collection of insect larvae, as the larvae are automatically separated from the eggs when they fall through the open bottom. Hence, the larvae can be easily harvested.

When the larvae are hatched and have fallen into the larvae collection crate, the larvae may be harvested and collected to rear the larvae. This may be done in the larvae collection crate, the contents of different larvae collection crates may be added in a one larvae collection crate, or the larvae may be removed from the larvae collection crates after harvest, e.g. being placed in a larvae rearing crate. When a larvae collection crate is emptied following harvest, it may be placed below the hatching stack again, e.g. the same hatching stack, or, when more than one hatching stack is present, a different hatching stack.

Preferably, at least two larvae collection crates are arranged below each hatching stack, wherein the larvae collection crates may be arranged directly on top of each other, or for example arranged in a rack, the top crate of the two larvae collection crates for example defining a first larvae collection crate and the bottom crate of the two larvae collection crates for example defining a second larvae collection crate. When the first larvae collection crates is removed from the stack, e.g. after a part of the eggs in the hatching egg crates have hatched, the remaining second larvae collection crate can still be used to collect larvae.

When the removed first larvae collection crate is then emptied, it may again be placed below the second, remaining larvae collection crate, such that the second larvae collection crate has become the top crate of the two larvae collection crates and the first larvae collection crate has become the lower crate. Preferably, this process can be repeated endlessly, wherein preferably all larvae collection crates of all hatching stacks in the insect breeding system, when the insect breeding comprises more than one hatching stack, are mutually interchangeable.

In embodiments, the hatching egg crates of the hatching stack may comprise eggs of essentially the same age, e.g. each hatching egg crate containing eggs laid on the same day or within the same time span of for example 12 hours or 24 hours or 48 hours, or eggs of a different age being arranged in one hatching egg crate. Preferably the hatching egg crates comprising older eggs are arranged more towards a bottom of the hatching stack, with a larvae collection crate below the hatching egg crates. In other embodiments, the hatching stack may comprise multiple egg crates that each contain eggs that are of a same age, e.g. all laid on the same day or within a time period of 24 or 48 hours. The hatching stack may then comprise, seen from a top of the stack, two, three, or more hatching egg crates stacked on top of each other, with a larvae collection crate below the hatching egg crates, in a repeated pattern. For example, the hatching stack may comprise three hatching egg crates with a larvae collection crate below them, then again three hatching egg crates with a larvae collection crate below them, and again three hatching egg crates and a larvae collection crate below.

In embodiments, a height of the hatching egg crates may be equal to or larger than a height of the larvae collection crates. Preferably, the larvae collection crates have a sufficient height to prevent larvae to climb out of the crates.

In embodiments, the larvae crates and/or the mother crates have smooth or very smooth inner walls, to prevent the larvae and/or the mothers to climb out of the crate and escape.

In embodiments, the eggs may be contained in spawn structures and the hatching egg crate may be configured to hold a multitude of said spawn structures. For example, the hatching egg crate may comprise a pair of spawn structure hangers including hanging slots, the hanging slots being configured to receive spawn structures, such that the spawn structures hang in the hanging slots. For example, the spawn structures described in WO 2017007310 A1 may be used.

In an embodiment, the egg crates, e.g. the hatching egg crates, are modified in that they are substantially bottomless, i.e. substantially the entire bottom of the egg crates may be removed, or the egg crates may be produced without a bottom. Small bottom structures, arranged at an inner side at a bottom of a wall of the egg crate may however be present. A substantially bottomless hatching egg crate ensures that hatched baby larvae, e.g. crawling out of the spawn structure, fall from the hatching egg crate into the larvae collection crate, without obstructions.

In embodiments, the bottom of the hatching egg crates comprises a lattice structure, wherein openings between the lattice structure are sized to allow the passage-through of hatched baby larvae. For example, the eggs in the hatching eggs crates may stick to the lattice structure, the eggs being contained or retained in the hatching egg crates. When a larvae hatches from an egg, it will move about in the hatching egg crate and fall through an opening in the lattice structure, into the larvae collection crate. In another example, or simultaneously, the hatching egg crate has a lattice structure to make it stronger and provide it with more rigidity, still allowing hatched larvae to fall through openings in the lattice structure and into the larvae collection crate.

In an embodiment, the closed bottom structure of the larvae collection crate is embodied as a slidable plate, configured to receive the hatched baby larvae. A slidable plate allows for easy collection of hatched larvae collection crate. Preferably, the larvae collection crate comprises multiple slidable plates, such that, when a top plate is removed from the larvae collection crate to harvest the larvae collected therein, baby larvae can still be collected in a lower slidable plate.

Preferably, the slidable plate spans the entire cross-sectional area of the larvae collection crate.

In an embodiment, the closed bottom structure of the larvae collection crate is tilted or tiltable with respect to a horizontal orientation, e.g. being arranged or able to be arranged at an angle of between 5 deg and 15 deg with respect to the horizontal orientation, and the larvae collection crate comprises a slotted opening, to allow for the automatic collection of baby larvae, from the larvae collection crate.

A tubing system may be attached to the stack of crates or the stacks of crates, said tubing system collecting the hatched larvae and transporting them to a central collection area.

In an embodiment, the insect breeding system comprises a spawning stack including a multitude of insect crates and at least one egg crate, wherein the insect crates are embodied as open-bottomed insect crates, modified in that they have an open bottom structure, wherein the egg crate is embodied as a collection egg crated, having a closed bottom structure, and wherein the collecting egg crate is arranged below an open-bottomed insect crate, such that eggs, laid by mother insects contained in the open-bottomed insect crates, fall through the open bottom structure of the open-bottomed insect crate, said eggs being collected in the collecting egg crate.

An advantage of this embodiment is that it allows for very efficient collection of insect eggs, as the eggs are automatically separated from the mothers contained in the insect crate when they fall through the open bottom. Hence, the eggs can be easily harvested.

For example, a multitude, e.g. two or three, open-bottomed insect crates may be stacked stacked on top of each other, the collecting egg crate being arranged below the open-bottomed insect crates, the stack comprising a larger number of insect crates than egg crates. For example, a collecting egg crate may be arranged below each open-bottomed insect crate, the stack comprising an equal number of egg crates and insect creates.

For example, the open bottom structure of the open-bottomed insect crates may comprise a sieve bottom or a lattice structure having perforations, on which trays are placed for the retainment of insect food. Insect food may also and/or alternatively be retained in a tray that is attached to a wall of the open-bottomed insect crate.

The spawning stack with open-bottomed insect crates and a collection egg crate makes use of the same inventive concept as the hatching stack with an open-bottomed hatching egg crate and a larvae collection crate, both stacks comprising two types of crates, each being suited for a different, consecutive, life cycle stage of an insect. The hatching stack comprises eggs and larvae, while the spawning stack comprises adult insects and eggs. In both stacks, the upper crates comprise a first life cycle stage, from which a consecutive life cycle stage results. The resulting life cycle stage falls out of the upper crates, into a lower crate, from which the resulting life cycle stage can be collected. In the case of the spawning stack, eggs fall from an upper open-bottomed insect crate into a lower egg collection crate, while in the case of the hatching stack, the larvae fall from an upper hatching egg crate into a lower larvae collection crate.

In an embodiment, the insect breeding system comprises a multitude of insect crates and at least one egg crate, wherein the insect crates are embodied as bottomed insect crates, wherein the egg crate is embodied as a hatching egg crate for the hatching of said insect eggs into baby larvae, the hatching egg crates preferably being modified in that they have an open bottom structure.

In embodiments, the bottomed insect crate comprises an opening in the bottom, e.g. covered with a sieve, e.g. for the easy removal of excrements produced by the adult insects.

In an embodiment, the insect breeding system comprises a spawning stack with a multitude of insect crates that are embodied as bottomed insect crates, and a hatching stack with a multitude of egg crates that are embodied as hatching egg crates for the hatching of said insect eggs into baby larvae, the hatching egg crates being modified in that they have an open bottom structure. Preferably, a larvae collection crate is arranged below said hatching stack, in a way as described in the above.

In an embodiment, the bottomed insect crate comprises a plurality of spawn structures, in which mother insects spawn their eggs, wherein the bottomed insect crate is modified in that it is configured to hold the spawn structures in a longitudinal direction of the bottomed insect crate, said spawn structures being dimensioned such that there is a space between respective outer ends of the spawn structure and side walls of the bottomed insect crate, and wherein the hatching egg crate is configured to receive the spawn structures in a lateral direction of the hatching egg crate. Hence, the width and the length of the similar, stackable crates is sized to allow the spawn structures to be placed in the longitudinal direction when the crate is modified for a first type of use, i.e. when the crate is modified to be an insect crate, and to allow the spawn structures to be placed in a lateral direction when the crate is modified for a second type of use, i.e. when the crate is modified to be a hatching egg crate. Preferably, the spawn structures are held at their bottom end when placed in the insect crates.

An advantage of dimensioning the spawn structures and the insect crates such that there is a space between the spawn structures and the side walls of the insect crate is that it prevents crawling insects to escape from the insect crate when they have climbed on the spawn structure.

In embodiments, the bottomed insect crate comprises spawn structure holders, arranged at the bottom of the bottomed insect crate, and configured to hold the spawn structures at their bottom end, wherein the spawn structures are preferably arranged in a substantially vertical orientation. It is noted that the hatching egg crates are modified to have an open bottom structure, and that the spawn structures, in contrast to when they are placed in the insect crates, may not be held at their bottom end. Hence, the spawn structures are held in a first way when arranged in the bottomed insect crate, and held in a second way when arranged in the open-bottomed hatching egg crate, the first way and the second way being different.

In an embodiment, the hatching egg crate comprises a pair of spawn structure hangers including hanging slots, the hanging slots being configured to receive the spawn structures such that the spawn structures hang in the hanging slots.

A spawning configuration may be defined for the spawn structures, in which the spawning structures are configured to allow optimal spawning of eggs by egg-laying mother insects. A further hatching configuration may be defined for the spawn structures, in which the spawn structure is configured to allow optimal separation of hatched baby larvae from the spawning structure. For example, in the hatching configuration the spawn structure, larvae may easily fall out of the spawn structure.

In an embodiment, the insect crate, the larvae crate, and the egg crate have mutually different colours, to make an easy distinguishing between the different types of crates possible.

In embodiments, the insect breeding system comprises multiple identical egg crates and/or multiple identical larvae crates and/or multiple identical insect crates.

In embodiments, the same crates are stacked directly on top of each other.

In embodiments, only two of the three types of crates (egg crate, insect crate, larvae crate) are part of the insect breeding system.

The invention further relates to a method for the breeding of insects, wherein use is made of an insect breeding system as disclosed in the above.

BRIEF DESCRIPTION OF THE DRAWINGS

The invention is further elucidated in relation to the drawings, in which:

FIG. 3B schematically shows a top view of a first embodiment of an insect crate according to the invention;

FIG. 3C schematically shows a top view of an embodiment of an egg crate according to the invention;

FIG. 3E schematically shows a side view of an embodiment of a crate according to the invention;

FIG. 4A schematically shows an isometric view of an embodiment of a hatching egg crate according to the invention, partially filled with spawn structures;

FIG. 4B schematically shows an isometric view of an embodiment of spawn structure holders according to the invention;

DETAILED DESCRIPTION OF EMBODIMENTS

Figure 1:
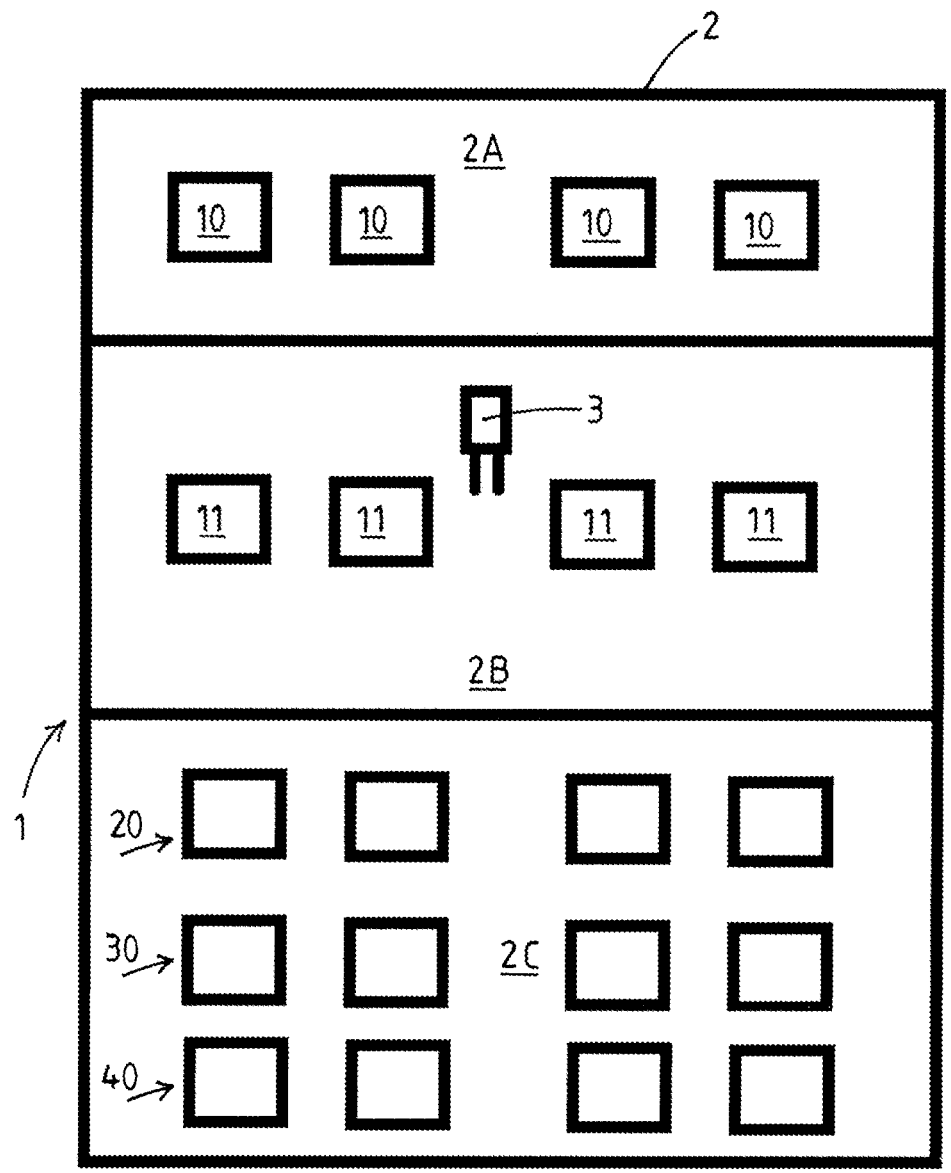
FIG. 1 schematically shows a cross-sectional top view of an embodiment of a climate housing according to the invention.

With reference to FIG. 1, an insect breeding system 1 for the breeding of insect larvae is shown. The insect breeding system 1 comprises a multitude of similar, stackable crates 20, 30, 40, a climate housing 2, and crate stacking equipment 3.

Figure 6:
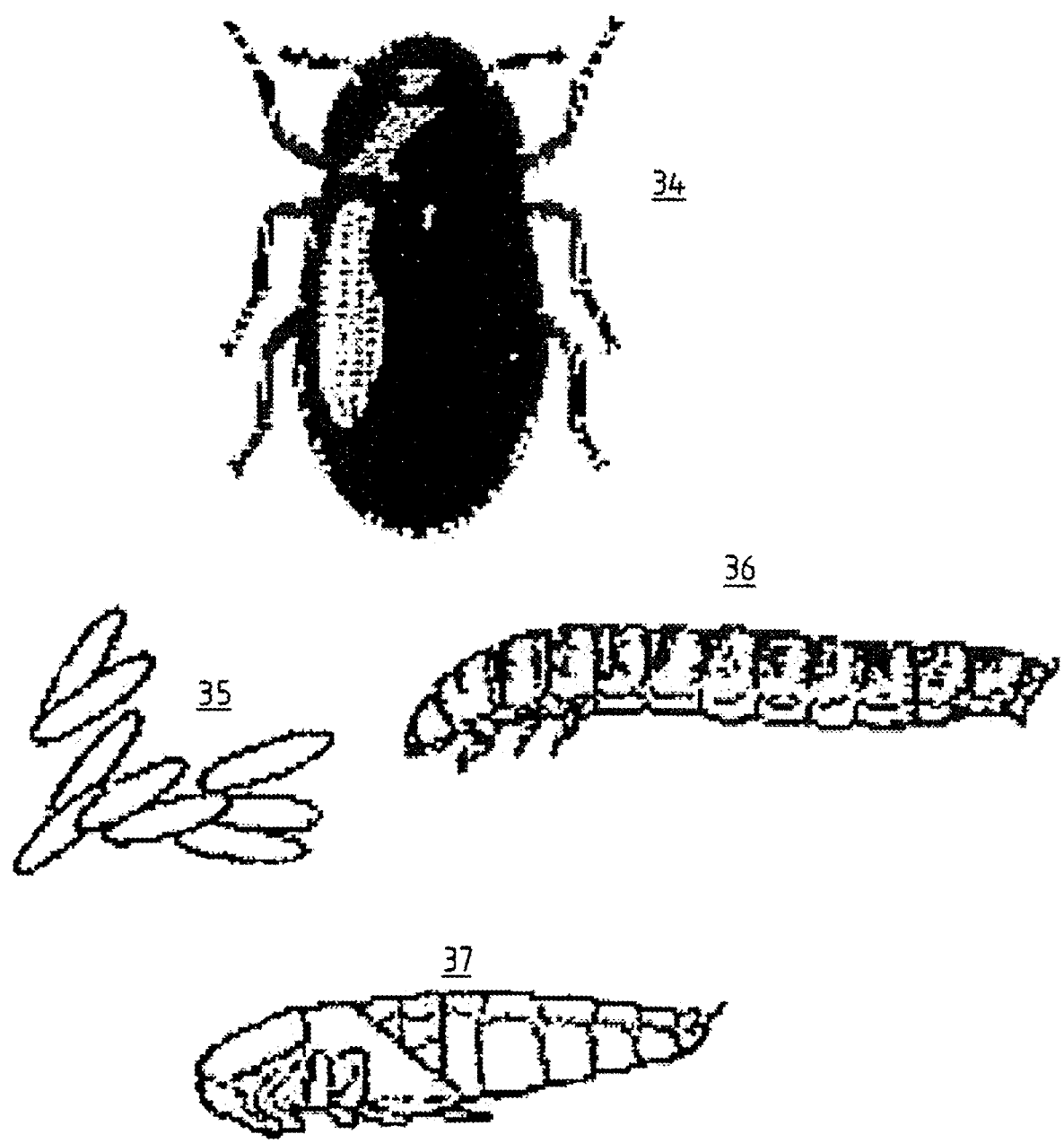
FIG. 6 schematically shows different life cycle stage of insects.

Four life cycle stages can be identified for most types of insects; which are shown in FIG. 6. Mother insects 34 lay eggs 35, which eggs 35 define a first life cycle stage. From the eggs 35, baby larvae 36 are born, which baby larvae 36 define a second life cycle stage. These baby larvae 36 grow into mature larvae, a process that in the art is called rearing, and ultimately become cocoons or pupae 37, defining the third life cycle stage. From a cocoon 37, an adult insect 34 pops, the adult insects 34 defining the fourth life cycle stage.

As can be seen in FIG. 1, the climate housing 2 comprises different chambers 2A, 2B, 2C, here three, in which the crates 20, 30, 40 are provided, preferably in stacks 10, 11. A first chamber 2A comprises four hatching stacks 10, a second chamber 2B comprises four spawning stacks 11, and a third chamber 2C comprises a multitude of crates 20, 30, 40, which may be empty and which chamber 2C may for example function as a storage chamber. The different chambers 2A, 2B, 2C may experience different environmental conditions, e.g. in terms of temperature and/or humidity. The climate housing 2 may comprise more than three chambers and may comprise more or many more stacks, e.g. up to a hundred or even (much) more, up to 10.000 or more for industrial-size insect breeding facilities or farms.

The crate stacking equipment 3 allows each of the same crates 20, 30, 40 to be arranged as a part of the one or more stacks 10, 11, e.g. on top of a stack 10, 11 or below a stack 10, 11, individually and independently, in a manner that will be described in more detail further below.

Figure 2A:
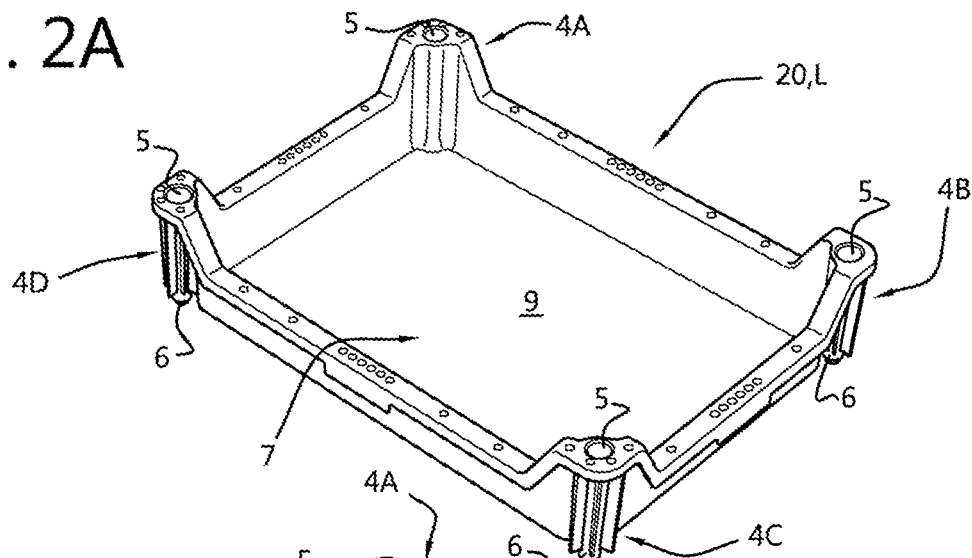
FIG. 2A schematically shows an isometric view of an embodiment of a larvae crate according to the invention.
Figure 2B:
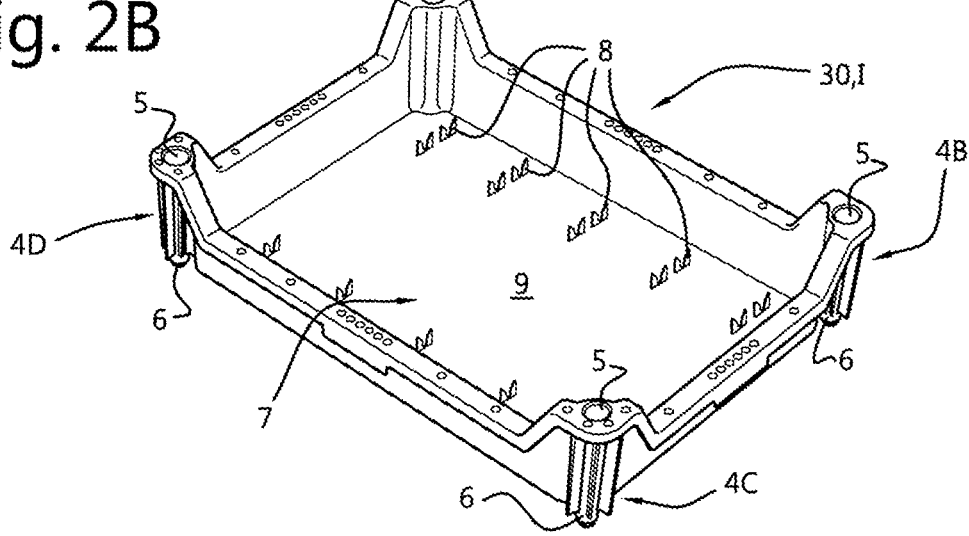
FIG. 2B schematically shows an isometric view of an embodiment of an insect crate according to the invention.
Figure 2C:
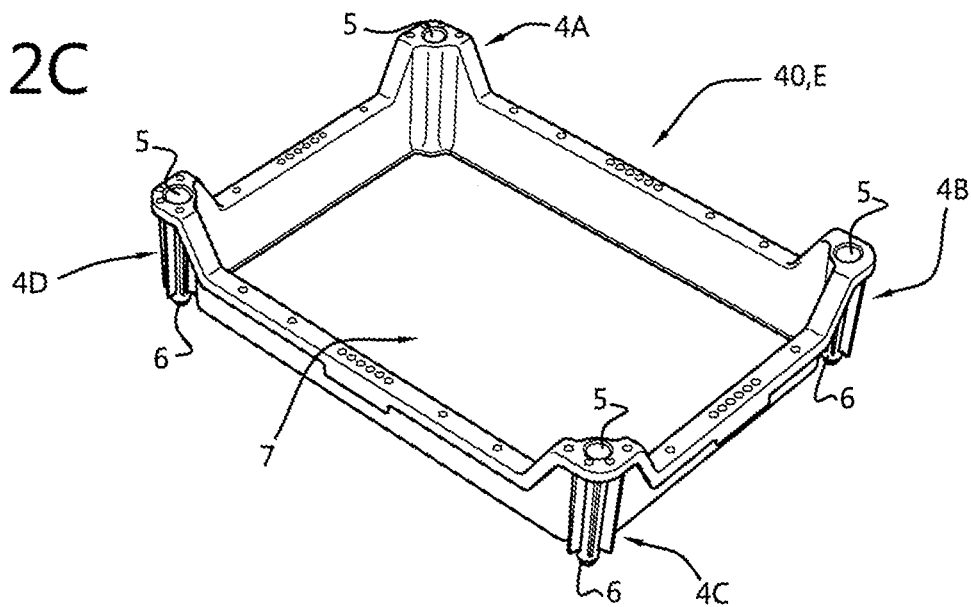
FIG. 2C schematically shows an isometric view of an embodiment of an egg crate according to the invention.

With reference to FIGS. 2A-2C, three types of crates 20, 30, 40 are shown. A first type of crate 20 is a larvae crate L, a second type of crate 30 is an insect crate I, and a third type of crate 40 is an egg crate E. The crates L, I, E are similar and stackable, each having a same width, indicated in FIGS. 3A-3D, a same length, also indicated in FIGS. 3A-3D, a same corner structure 4 that comprises complementary lower elements 5 and upper elements 6, configured to allow stacking of the crates 20, 30, 40 on top of each other by allowing the upper elements 6 of a lower crate 20, 30, 40 to interact with lower elements 6 of an upper crate 20, 30, 40, and a containment area 7 defined by the width, the length, and a height of the crate 20, 30, 40. The insect breeding system comprises a multitude of said similar stackable crates 20, 30, 40. The crates may be those described in pending application NL 2019079, in the name of the same applicant.

The similar and stackable crates 20, 30, 40 can be distinguished into at least three types of crates: an egg crate E, a larvae crate L, and an insect crate I. Therefore, the crates 20, 30, 40 can for example be provided with suitable holders 8, and/or can be modified in that at least a part of a bottom 9 thereof is removed, such that each crate 20, 30, 40 can be tuned to one of the said crate types E, I, L.

The egg crate E is suited to contain insect eggs in the containment area 7 thereof, e.g. to allow the hatching of said insect eggs into baby larvae.

The larvae crate L is suited to contain larvae, e.g. baby larvae, and larvae food in the containment area 7 thereof, allowing the rearing of such larvae 36.

The insect crate I is suited to contain live adult insects including mother insects and insect food in the containment 7 area thereof, allowing the mothers to lay eggs.

The insect breeding system 1 preferably comprises all three of the mentioned crate types E, L, I, but at least two of the three crate types E, I, L are part of the insect breeding system 1.

It may be preferred when the different types of crates E, I, L, e.g. the three different types of crates, have mutually different colours.

FIGS. 3A-3D show top views of the different crate types E, I, L, where it can well be observed that they all have same lengths D2 and widths D1.

Figure 3A:
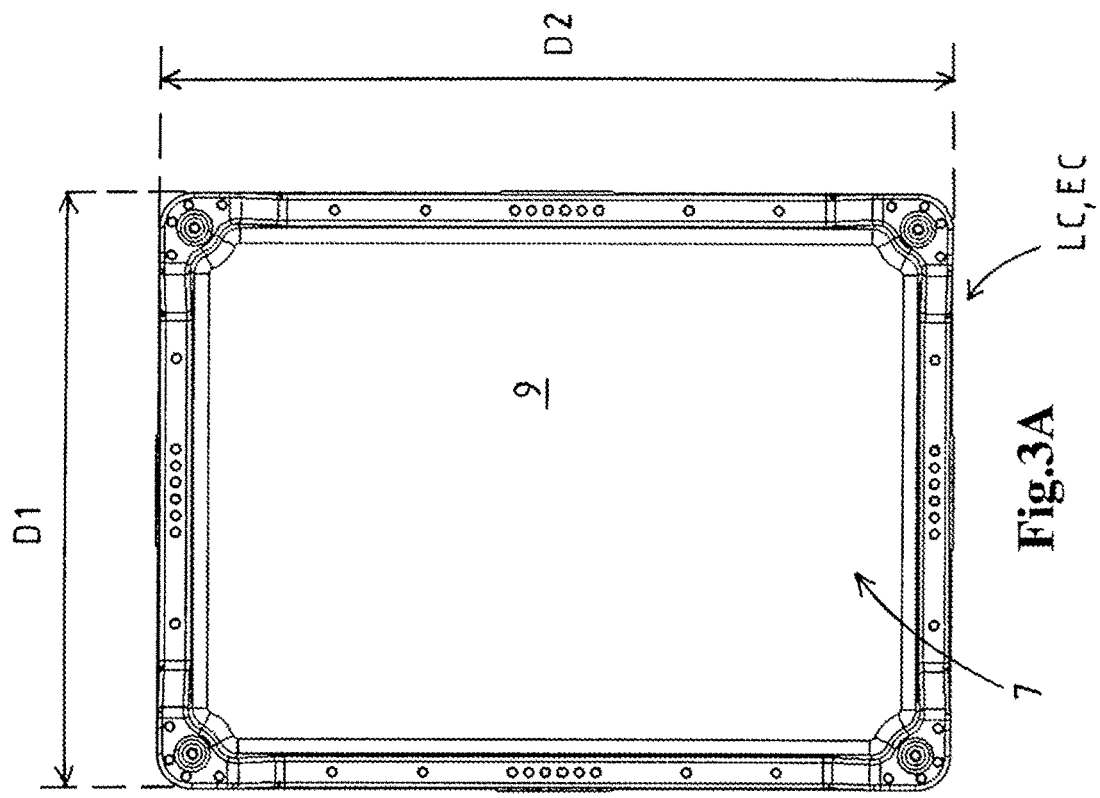
FIG. 3A schematically shows a top view of an embodiment of a larvae crate according to the invention.

The crate LC, EC shown in FIG. 3A has a closed bottom 9. This allows it to be used as a larvae collection crate LC or as an egg collection crate EC. A larvae collection crate LC is a larvae crate L having a closed bottom structure. An egg collection crate EC is an egg crate E having a closed bottom structure.

The crate BI shown in FIG. 3B is modified in that it has a bottom 9 that is partially opened. More specifically, the crate BI is a bottomed insect crate I, that has a bottom 9 with an opening 9A in it. The bottom opening 9A is here covered with a sieve and allows excrements of the insects to be removed from the bottomed insect crate BI.

The bottomed insect crate BI is configured to hold adult insects in it, and allows mother insects to lay eggs. For certain types of insects, e.g. beetles, such as lesser mealworms (formally known as Alphitobius diaperinus, a species of beetle in the family Tenebrionidae) or zophobas morios (which larvae are known as superworms or zophobas), it may be preferred to provide so-called spawn structures in the bottomed insect crate BI to stimulate mothers to lay eggs. Therefore, spawn structure holders 8 are provided in the bottomed insect crate BI. The bottomed insect crate BI is configured to contain a plurality, here four, of spawn structures, in which mother insects spawn their eggs. As can be seen, the bottomed insect crate BI is modified in that it is configured to hold the spawn structures in a longitudinal direction of the bottomed insect crate BI, said spawn structures being dimensioned such that there is a space 16, 17, 18, when the spawn structure is placed inside the containment area 7, between respective ends of the spawn structure and side walls 19, 20, 21, 22 of the bottomed insect crate BI.

The crate HE shown in FIG. 3C has an open bottom structure. More specifically, the crate HE is an open-bottomed hatching egg crate HE for the hatching of insect eggs into baby larvae, the hatching egg crate HE being modified in that it has an open bottom structure. More specifically, in the shown embodiment, the hatching egg crate HE is substantially bottomless.

The hatching egg crate HE shown in FIG. 3C is empty, i.e. it does not contain any eggs. A hatching egg crate HE filled with eggs, here stored in spawn structures 15, is shown in FIG. 4A. Here, the hatching egg crate HE comprises a pair of spawn structure hangers 8' including hanging slots 24, the hanging slots 24 being configured to receive the spawn structures 15 such that the spawn structures 15 hang in the hanging slots 24.

An isometric, isolated view of an embodiment of the spawn structure hangers 8' is shown in FIG. 4B. The hanging slots 24 are here clearly visible.

By providing spawn structure hangers 8', the hatching egg crate HE is configured to receive spawn structures 15 in a lateral direction of the hatching egg crate HE.

Figure 3D:
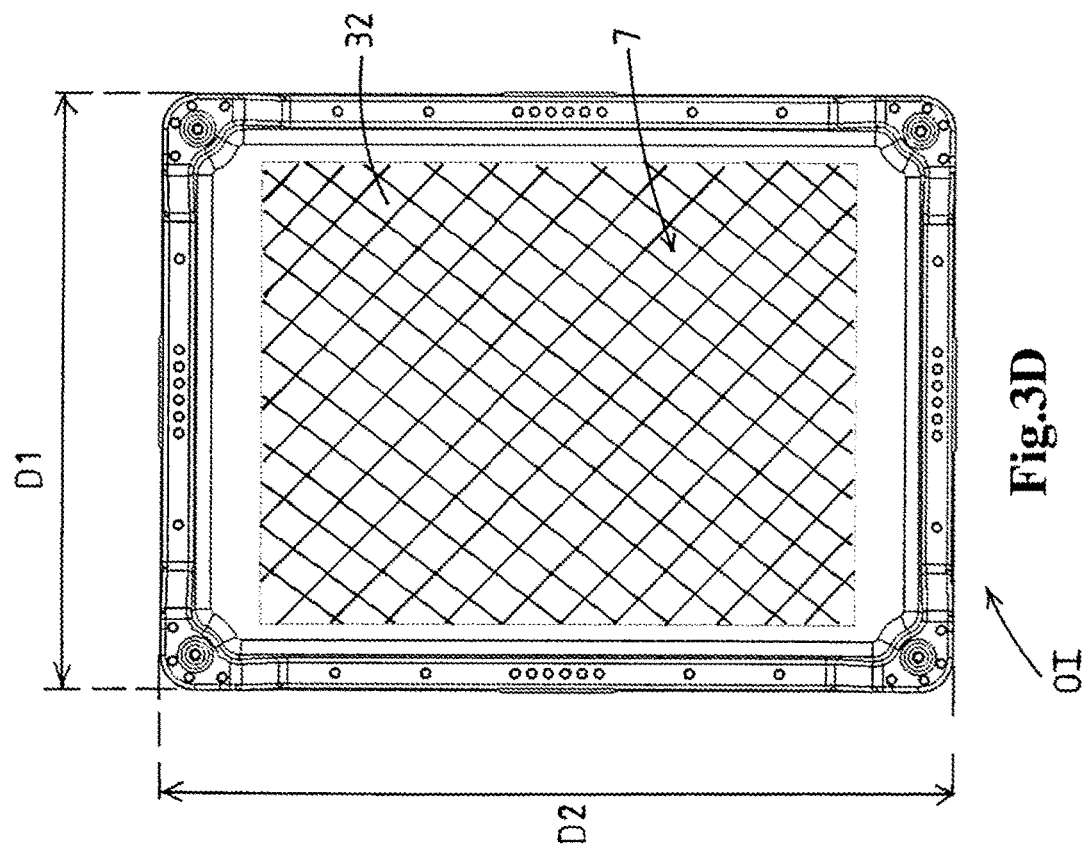
FIG. 3D schematically shows a top view of a second embodiment of an insect crate according to the invention.

The crate OI shown in FIG. 3D has an open bottom structure. More specifically, the crate OI is an open-bottomed insect crate OI, an insect crate I modified in that is has an open bottom structure. More specifically, the open-bottomed insect crate OI comprises a sieve bottom 32.

FIG. 3E shows an exemplary side view of a crate. Note that the shape of the side panel 19 of the crates E, I, L may be different and needs not be the same for all crates E, I, L.

The different types E, I, L of the similar stackable crates 20, 30, 40, and the different embodiments HE, EC, LC, BI, OI of these types E, I, L allow to provide different stacks of crates. For example, a stack of egg crates E may be provided. For example, a stack of insect crates I may be provided. For example, a stack of larvae crates L may be provided. For example, different types of crates E, I, L may be mixed in a stack, said stack comprising two or three types of crates E, I, L.

An exemplary stack 10 is shown in FIGS. 5A and 5E, the stack 10 comprising a multitude of hatching egg crates HE and two, i.e. at least one, i.e. a multitude of larvae collection crates LC. This stack may be defined as a hatching stack 10.

Hence, the hatching stack 10 comprises a multitude of crates modified in that they have an open bottom structure, i.e. the hatching egg crates HE, and at least one collection crate, i.e. the two larvae collection crate LC, having a closed bottom structure, allowing insects of a particular life cycle, arranged in the open-bottomed crates, i.e. baby larvae when hatched from the eggs in the hatching crates, to fall through the open bottom structure of said open-bottomed crate, said insect of said life cycle being collected in the collection crate, i.e. the larvae collection crate LC.

Hence, the hatching stack 10 comprises a multitude of egg crates E, here hatching egg crates HE, and at least one larvae crate L, here two larvae collection crates LC, wherein the hatching egg crates HE are arranged on top of each other and the larvae collection crate LC is arranged below said hatching egg crates HE, such that baby larvae hatching from the eggs contained in the hatching egg crates HE are able to fall through the open bottom structure of the multitude of stacked hatching egg crates HE, said baby larvae being collected in the larvae collection crate LC, e.g. on the closed bottom structure thereof.

In the embodiment of FIG. 5A, the larvae collection crate LC is similar to the crate shown in FIG. 3A, having a closed bottom.

In the embodiment of FIG. 5E, the closed bottom structure of the larvae crate LC is embodied as a slidable plate 13 comprising a handle 13A, the slidable plate 13 being configured to receive the hatched baby larvae. Here, the larvae crate LC comprises three slidable plates 13, although any number of slidable plates 13 is conceivable.

Not shown, but envisioned, is that the closed bottom structure of the larvae collection crate LC is tilted or tiltable with respect to a horizontal orientation, e.g. being arranged or able to be arranged at an angle of between 5 deg and 15 deg with respect to the horizontal orientation, and wherein the larvae collection crate LC comprises a slotted opening, preferably at the lowest point thereof, to allow for the automatic collection of baby larvae, e.g. hatched baby larvae, from the larvae collection crate LC.

Figure 5B:
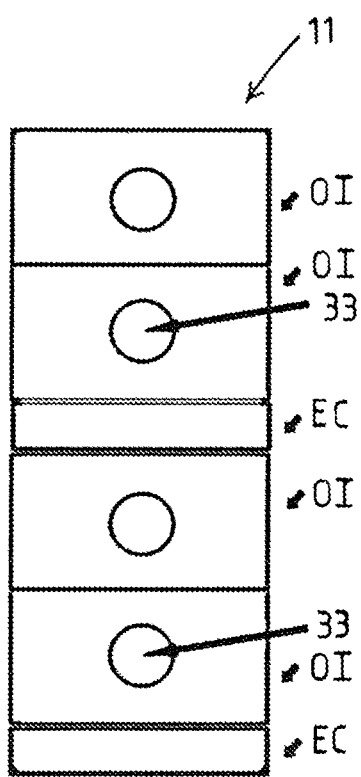
FIG. 5B schematically shows a frontal view of a second embodiment of a stack of crates according to the invention.
Figure 5C:
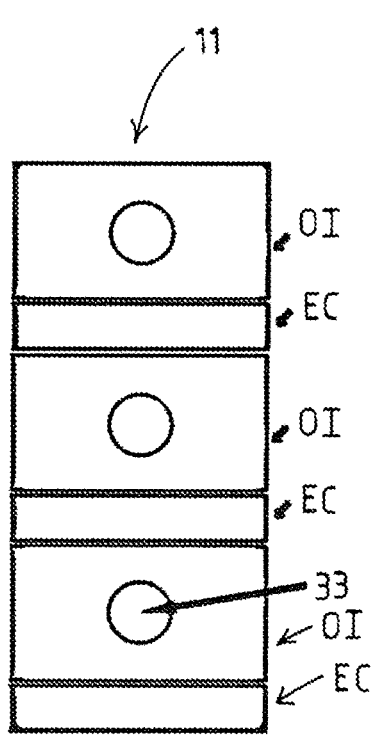
FIG. 5C schematically shows a frontal view of a third embodiment of a stack of crates according to the invention FIG. 5D schematically shows a cross-sectional view of the stack of crates according to FIG. 5B and/or FIG. 5C.

A further exemplary stack 11 is shown in FIG. 5B and FIG. 5C, the stack 11 comprising a multitude of insect crates I, here open-bottomed insect crates OI and at least one egg crate E, here egg collection crates EC. This stack may be defined as a spawning stack 11.

Hence, FIGS. 5B and 5C disclose a spawning stack 11 comprising a multitude of crates, here insect crates I, modified in that they have an open bottom structure, here open-bottomed insect crates OI, and at least one collection crate, here egg crates E, more specifically egg collection crates E having a closed bottom structure, allowing insect of a particular life cycle, here eggs, arranged in the open-bottomed crates, e.g. after the eggs are spawned by mother insect, to fall through the open bottom structure thereof, said insect of said life cycle being collected in the egg collection crate EC.

The open-bottomed insect crates OI may comprise an air inlet 33 to allow fresh oxygen to enter the open-bottomed insect crate OI. In embodiments, e.g. when the crate comprises flying insects, it may be preferred when the air inlet 33 is covered with a sieve to prevent escape of the insects.

Hence, FIGS. 5B and 5C disclose a spawning stack 11 comprising a multitude of insect crates I, here open-bottomed insect crates OI and at least one egg crate E, here egg collection crates EC, wherein the egg collection crate EC is arranged below an open-bottomed insect crate OI, such that eggs, laid by mother insects contained in the open-bottomed insect crates OI, fall through the open bottom structure of the f open-bottomed insect crates OI, said eggs being collected in the egg collection crate EC. The mother crates may for example comprise cockroaches.

The spawning stack 11 of FIG. 5B comprises a multitude of open-bottomed insect crates OI, here two, stacked on top of each other, with an egg collection crate EC arranged below said stacked open-bottomed insect crates OI.

The spawning stack 11 of FIG. 5C comprises a multitude of open-bottomed insect crates OI, with an egg collection crate EC arranged below each open-bottomed insect crate OI.

Figure 5D:
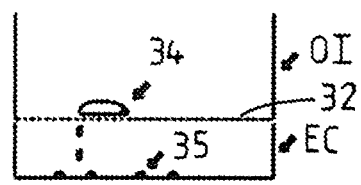
FIG. 5A schematically shows a frontal view of a first embodiment of a stack of crates according to the invention.
FIG. 5E schematically shows a frontal view of a fourth embodiment of a stack of crates according to the invention.

FIG. 5D shows a longitudinal or lateral cross-sectional view of two crates OI, EC of the stacks 11 shown in FIGS. 5B and 5C. An open-bottomed insect crate OI is arranged on top of the egg collection crate EC. Visible is the sieve bottom 32 of the open-bottomed insect crate OI. Also visible are eggs 35, spawned by a mother insect 34, which eggs fall through the sieve bottom 32 of the open-bottomed insect crate OI, and into the egg collection crate EC.

The stack of similar stackable crates may further comprise a multitude of insect crates I, e.g. bottomed insect crates OI, and at least one egg crate E, e.g. a hatching egg crate HE. The egg crate or crates E are then preferably arranged on top of the insect crates I, but may also be arranged below the insect crates I.

The stack of similar stackable crates may further comprise a spawning stack with a multitude of insect crates I, e.g. insect crates I that are embodied as bottomed insect crates BI. The insect breeding system 1 may further comprise other stacks than described in the above. The insect breeding system 1 may comprise a multitude of the stacks described in the above, e.g. multiple stacks of the same or a similar configuration, and/or multiple stacks of different configurations. Similar stacks may for example be stacks that comprise the same crate types, but in different numbers, and/or varying in stack height.

As shown, each stack 10, 11, has a stack height of at least five crates. Preferably, each stack 10, 11 has a stack height of at least eight crates, such as ten crates.

The invention further relates to a method for the breeding of insects, wherein use is made of an insect breeding system as described in the above.

With reference again to FIG. 1, in use, the crate stacking equipment 3 may be configured to remove a bottom crate or a crate arranged near a bottom of a stack, e.g. a hatching egg crate, from the stack of crates, and may be configured to place the removed crate on top of a stack, e.g. the same stack or a different stack.

The removed crate may be a hatching egg crate configured to hold spawn structures. The spawn structures may then be emptied of eggs before the hatching egg crate is removed from the stack, all or substantially all eggs having hatched. The empty spawn structures may then be removed from the hatching egg crate, e.g. manually or with robots, and harvested spawn structures, i.e. spawn structures removed from bottomed insect crates, in which mother insect have spawned their eggs, may be placed in the hatching egg crate, either manually or with a robot, before placing the removed crate on top of a stack.

When the emptied spawn structures are removed from the hatching egg crates, they may be placed in a bottomed insect crate, which bottomed insect crates may consecutively be stacked.

The invention claimed is:

1. An insect breeding system for the breeding of insect larvae, comprising:
   a multitude of similar, stackable crates, a climate housing, and crate stacking equipment;
   wherein the multitude of similar, stackable crates each have:
      a same width;
      a same length;
      a same corner structure that comprises complementary lower elements and upper elements, configured to allow stacking of the crates on top of each other by allowing the upper elements of a lower crate to interact with lower elements of an upper crate;
      a containment area defined by the width, the length, and a height of the crate,
   wherein each crate is tuned to one of the following crate types, at least a part of a bottom of the crates being modified to tune the crates to mutually different crate types; and
   wherein the below three crate types are part of the insect breeding system:
      a hatching egg crate, suited to contain insect eggs in the containment area thereof, said hatching egg crate being open-bottomed and comprising holders for holding spawn structures;
      a larvae crate, suited to contain larvae, and larvae food in the containment area thereof, allowing the rearing of such larvae, said larvae crate being closed-bottomed;
      an insect crate, suited to contain live adult insects including mother insects and insect food in the containment area thereof, allowing the mothers to lay eggs, said insect crate being bottomed and comprising a plurality of spawns structures in which mother insects spawn their eggs;
   wherein the climate housing is provided with one or more stacks of said similar crates, each stack having a stack height of at least five; and wherein the crate stacking equipment is configured to handle each of the egg, larvae, and insect crate types to be arranged as a part of the one or more stacks, individually and independently.

2. Insect breeding system according to claim 1, wherein the stack comprises a multitude of crates having an open bottom structure, and at least one collection crate, having a closed bottom structure, allowing insects of a particular life cycle, arranged in the open-bottomed crates, to fall through the open bottom structure thereof, said insects of said life cycle being collected in the collection crate.

3. Insect breeding system according to claim 1, comprising a hatching stack with a multitude of egg crates and at least one larvae crate,
   wherein the egg crates are embodied as hatching egg crates for the hatching of said insect eggs into baby larvae, the hatching egg crates being modified in that the hatching egg crates have an open bottom structure,
   wherein the larvae crate is embodied as a larvae collection crate having a closed bottom structure, and
   wherein the hatching egg crates are arranged on top of each other and the larvae collection crate is arranged below said hatching egg crates,
   such that baby larvae hatching from the eggs contained in the hatching egg crates are able to fall through the open bottom structure of the multitude of stacked hatching egg crates, said baby larvae being collected in the larvae collection crate.

4. Insect breeding system according to claim 3, wherein the closed bottom structure of the larvae crate is embodied as a slidable plate, configured to receive the hatched baby larvae.

5. Insect breeding system according to claim 3, wherein the closed bottom structure of the larvae collection crate is tilted or tiltable with respect to a horizontal orientation, and wherein the larvae collection crate comprises a slotted opening to allow for the automatic collection of baby larvae from the larvae collection crate.

6. Insect breeding system according to claim 1, comprising a spawning stack including a multitude of insect crates and at least one egg crate,
   wherein the insect crates are embodied as open-bottomed insect crates, modified in that the insect crates have an open bottom structure,
   wherein the egg crate is embodied as a collection egg crated, having a closed bottom structure, and
   wherein the egg collection crate is arranged below an open-bottomed insect crate,
   such that eggs, laid by mother insects contained in the open-bottomed insect crates, fall through the open bottom structure of the open-bottomed insect crate, said eggs being collected in the collecting egg crate.

7. Insect breeding system according to claim 6, wherein the open-bottomed insect crate comprises a sieve bottom.

8. Insect breeding system according to claim 1, comprising a spawning stack with a multitude of insect crates that are embodied as bottomed insect crates, and a hatching stack with a multitude of egg crates that are embodied as hatching egg crates for the hatching of said insect eggs into baby larvae, the hatching egg crates being modified in that the hatching egg crates have an open bottom structure.

9. Insect breeding system according to claim 1,
   wherein the insect crate is configured to hold the spawn structures in a longitudinal direction of the insect crate, said spawn structures being dimensioned such that there is a space between respective ends of the spawn structure and side walls of the bottomed insect crate, and
   wherein the hatching egg crate is configured to receive the spawn structures in a lateral direction of the hatching egg crate.

10. Insect breeding system according to claim 1, wherein the hatching egg crate comprises a pair of spawn structure hangers including hanging slots, the hanging slots being configured to receive the spawn structures such that the spawn structures hang in the hanging slots.

11. Insect breeding system according to claim 1, wherein the insect crate, the larvae crate, and the egg crate have mutually different colours.

12. Insect breeding system according to claim 1, wherein each stack has a stack height of at least eight.

13. Insect breeding system according to claim 1, wherein the larvae crate is suited to contain baby larvae.

14. Method for the breeding of insects, comprising:
providing a multitude of similar, stackable crates, a climate housing, and crate stacking equipment;
wherein the multitude of similar, stackable crates each have:
- a same width;
- a same length;
- a same corner structure that comprises complementary lower elements and upper elements, configured to allow stacking of the crates on top of each other by allowing the upper elements of a lower crate to interact with lower elements of an upper crate;
- a containment area defined by the width, the length, and a height of the crate, wherein each crate is tuned to one of the following crate types; and
wherein the below three crate types are part of the insect breeding system:
- a hatching egg crate, suited to contain insect eggs in the containment area thereof, said hatching egg crate being open-bottomed and comprising holders for holding spawn structures;
- a larvae crate, suited to contain larvae, and larvae food in the containment area thereof, allowing the rearing of such larvae;
- an insect crate, suited to contain live adult insects including mother insects and insect food in the containment area thereof, allowing the mothers to lay eggs, said insect crate being bottomed and comprising a plurality of spawns structures in which mother insects spawn their eggs;

wherein the climate housing is provided with one or more stacks of said similar crates, each stack having a stack height of at least five; and wherein the crate stacking equipment is configured to handle each of the egg, larvae, and insect crate types to be arranged as a part of the one or more stacks, individually and independently.

* * * * *